US 9,339,176 B2

(12) United States Patent
Weinstein et al.

(10) Patent No.: US 9,339,176 B2
(45) Date of Patent: May 17, 2016

(54) TOOLS FOR TRANSORAL SURGERY

(75) Inventors: Gregory S. Weinstein, Gladwyne, PA (US); Bert W. O'Malley, Jr., Villanova, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/315,466

(22) Filed: Dec. 9, 2011

(65) Prior Publication Data
US 2012/0157787 A1  Jun. 21, 2012

Related U.S. Application Data

(60) Provisional application No. 61/459,615, filed on Dec. 15, 2010.

(51) Int. Cl.
*A61M 16/04* (2006.01)
*A61B 1/32* (2006.01)

(52) U.S. Cl.
CPC ........................................ *A61B 1/32* (2013.01)

(58) Field of Classification Search
USPC .................................................. 600/101–249
See application file for complete search history.

(56) References Cited

U.S. PATENT DOCUMENTS 5,896,491 A     4/1999  Englefield
5,897,491 A *   4/1999  Kastenbauer et al. ........ 600/239

OTHER PUBLICATIONS

Intuitive Surgical, "da Vinci Transoral Surgery: Procedure Guide," http://www.uphs.upenn.edu/pennorl/education/documents/daVinciTORSProcedureGuide.pdf, Rev. A, Aug. 2008, 32 pages.
The ENT-Group, "FK laryngo-pharyngoscope," http://www.gyrusmedical.de/fportal/docs/36, FK laryngo-pharynogoscope Brochure, Jan. 2003 edition, 40 pages.

* cited by examiner

*Primary Examiner* — Thomas J Sweet
*Assistant Examiner* — Samuel Hanna
(74) *Attorney, Agent, or Firm* — Baker & Hostetler, LLP (57) ABSTRACT

The invention is directed towards tools for use in performing surgery or examination via the oral cavity, in particular in the region of the oral cavity, oropharynx, larynx, and hypopharynx, devices and systems incorporating these tools, and procedures using these tools. More specifically, the tools, devices, systems and procedures are directed towards Transoral Robotic Surgery or any non-robotic transoral surgical approach.

23 Claims, 10 Drawing Sheets

TOOLS FOR TRANSORAL SURGERY

CROSS REFERENCE TO RELATED APPLICATIONS

This application claims priority to U.S. Provisional Application Ser. No. 61/459,615, filed Dec. 15, 2010, which is incorporated by reference herein in its entirety.

TECHNICAL FIELD

The invention is directed towards tools for use in performing surgery or examination via the oral cavity, in particular in the region of the oral cavity, oropharynx, larynx, and hypopharynx, devices and systems incorporating these tools, and procedures using these tools. More specifically, the tools, devices, systems and procedures are directed towards Transoral Robotic Surgery or any non-robotic transoral surgical approach.

BACKGROUND

Benign and malignant lesions, including lesions of the tongue, pharynx, and larynx, commonly occur in the oral cavity, pharynx and larynx which frequently require surgical removal. The most common malignancy of the mucosa or internal lining of the aforementioned structures is known as squamous cell carcinoma. Historically, these surgeries were done either with a very radical open surgical approach or by laser surgery. The former method is enormously invasive, requiring long recuperative times for the patient. The latter method suffers, among other things, from inherent problems of line-of-sight issues for the surgeon related to the fact that the optics, and most often the laser itself, are placed outside the mouth. In addition with traditional laser surgery the surgical tools allow for limited range of motion which limits the capability of the surgeon. Various retractors were developed to provide greater control of the instruments during such surgeries. Examples of such frames include the Feyh-Kastenbauer, Crowe-Davis, Davis-Geck, and Dingman retractors, each providing a slightly different design approach for the same or similar surgeries.

More recently, a technique referred to as TransOral Robotic Surgery ("TORS") has been developed by head and neck surgeons at the University of Pennsylvania School of Medicine and approved by the FDA, for TransOralotolaryngologic surgical procedures to treat benign tumors and select malignant tumors of the mouth, voice box, tonsil, tongue and other parts of the throat. The benefits of this type of surgery are significant: 45,000 Americans and approximately 500,000 people worldwide are diagnosed with head and neck cancers each year. Head and neck tumor treatments often involve a combination of surgery, radiation therapy, and chemotherapy. In many cases, surgery offers the greatest chance of cure, yet conventional surgery may require an almost ear-to-ear incision across the throat or splitting the jaw, resulting in speech and swallowing deficits for patients. In comparison, the minimally invasive TORS approach, which accesses the surgical site through the mouth, has been shown to improve long term swallowing function and reduce risk of infection while speeding up the recovery time. When compared to traditional surgeries, after their cancers have been removed successfully, patients have been able to begin swallowing on their own sooner and leave the hospital earlier. TORS outcomes are markedly improved when compared to standard chemotherapy, radiation or traditional open surgical approaches for oropharyngeal cancer.

Figure 1:
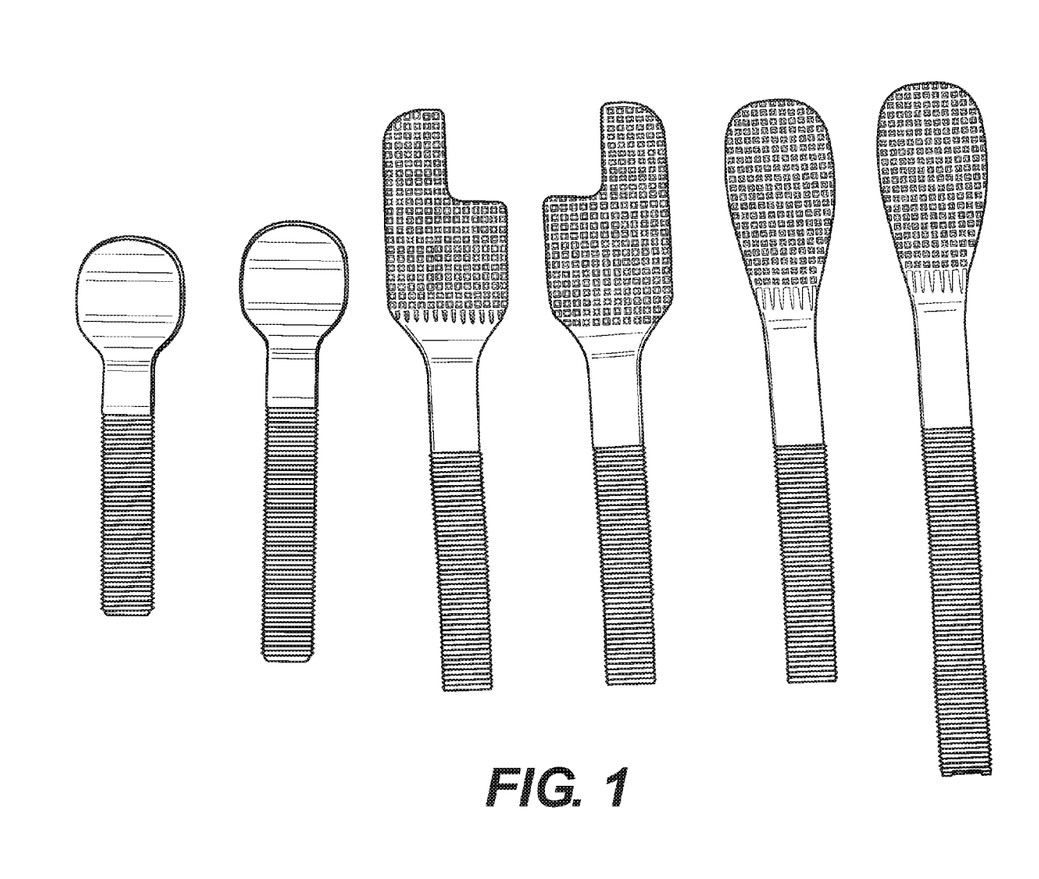
FIG. 1 shows a bottom side view of a range of labial-commissure spatulas historically applied to the FK retractor. The top surfaces of these spatulas to not contain the ratcheted teeth on the handle or the grid pattern on the blade
Figure 2A:
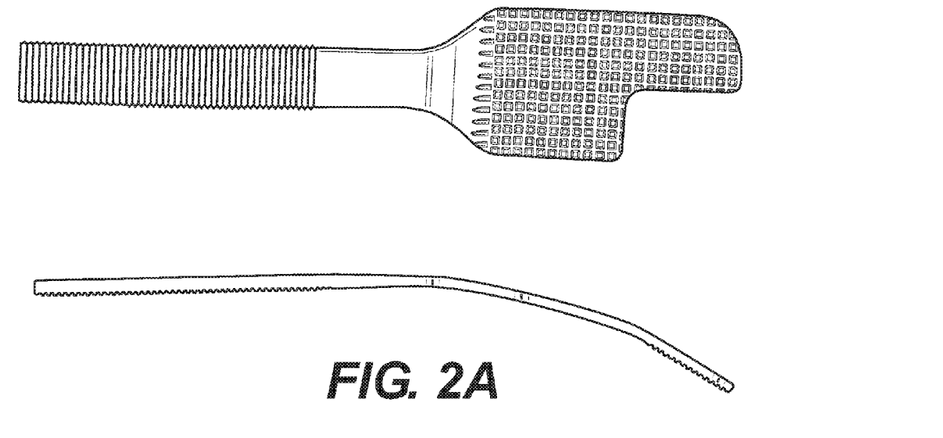
FIGS. 2A and 2B show bottom and side view orientations of two labial-commissure spatulas historically applied to the FK retractor.
Figure 2B:
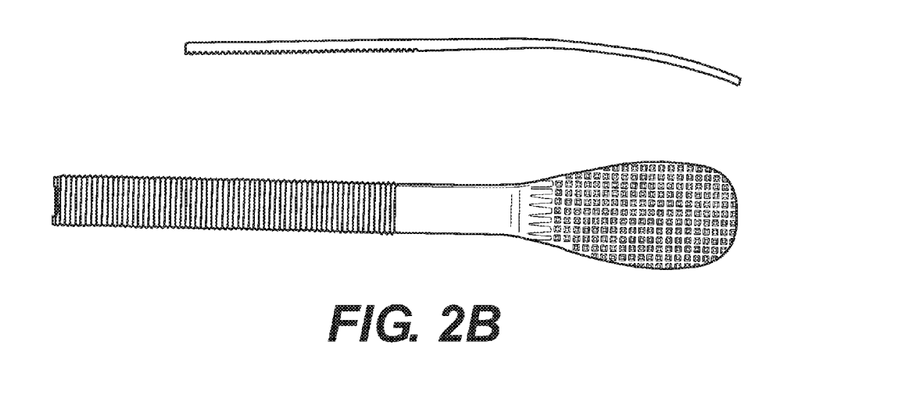
Figure 3A:
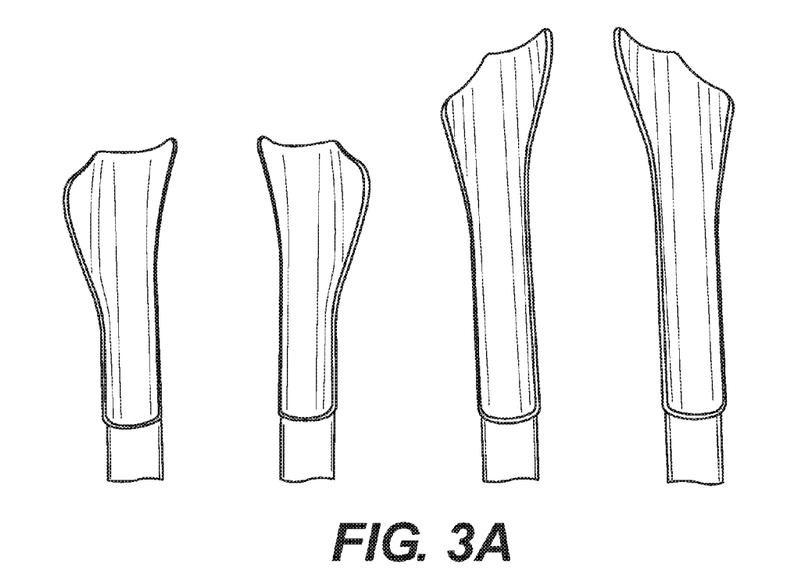
FIG. 3A shows the top view of two pairs of matched blades.
Figure 3B:
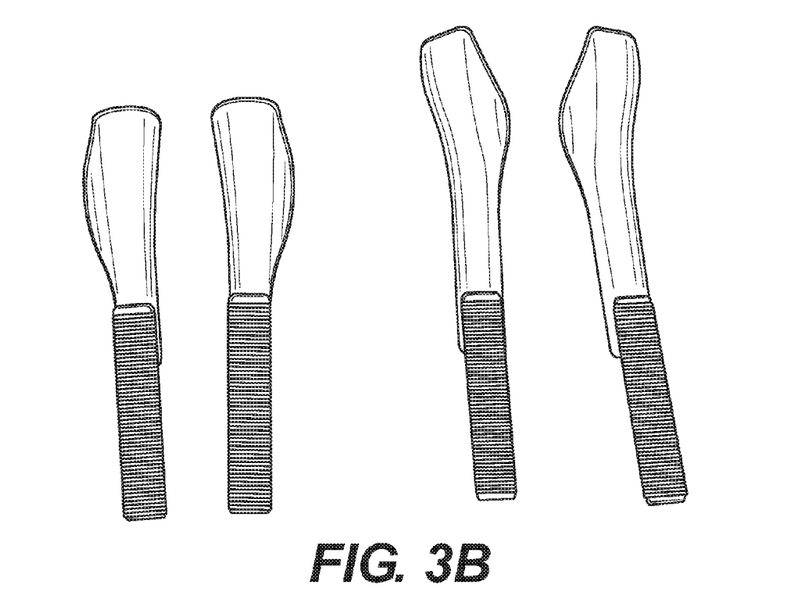
FIG. 3B shows the corresponding bottom view.

However, the present inventors discovered that conventional retractors and associated tools did not provide the line-of-sight or range of motion features necessary for TORS. U.S. Pat. No. 5,897,491 (the '491 patent), which is incorporated by reference herein, describes the so-called Feyh-Kastenbauer, or FK, retractor which initially appeared to be suited for this application. This retractor was useful for allowing better access for manually applied laser surgery and some other non-laser resections. But, as the present inventors found, significant limitations in commercial embodiments of this retractor existed, when applied to TORS, most notably the inability to adequately use the previous invention during robotic surgery. In particular, the frame of this retractor provided insufficient access to the patient's mouth for the robotic tools. Similarly, the present inventors discovered that the spatulas used to hold open the patient's mouth (described in the '491 patent as the labial-commissure spatula 5) provided insufficient access to the deeper portions of the patient's throat by the robotic arms. FIG. 1 and FIG. 2 show various embodiments and orientations of historically available spatulas for use with the FK retractor.

SUMMARY

The present inventions overcome the deficiencies of the prior art and are directed towards tools for use in performing surgery or examination via the oral cavity, in particular in the region of the oral cavity, oropharynx, larynx, and hypopharynx, devices and systems incorporating these tools, and procedures using these tools. More specifically, the tools, devices, systems and procedures are directed towards Transoral Robotic Surgery or any non-robotic transoral surgical approach.

One embodiment of this invention provides a spatula for use in surgery or examination via the mouth comprising: (a) a handle (10), having proximal and distal ends and a longitudinal axis between the ends; (b) a blade (20) having top and bottom surfaces, a proximal end (30), a distal end (40), and opposing lingual (50) and mandibular (60) edges; the distance between the proximal and distal edges defining blade length; the distance between opposing lingual and mandibular edges defining blade width; wherein (i) the proximal end of the blade being attached to the distal end of the handle, either directly or through use of a spacer, the entire assembly having a major longitudinal axis (70) parallel to the longitudinal axis of the handle and extending along the length of the blade; (ii) the blade being upwardly concave across the width, having a centerline (80) at the lowest line of concavity along the blade; (iii) the blade containing a region of curvature along its length, such that the blade depends downward while maintaining the upwardly concave curvature across the width; and (iv) each of the lingual and mandibular edges having a lobed protrusion, each lobe having a point of maximum lateral displacement from the body of the blade, asymmetrically displaced with respect to one another along the length of the blade, such that the mandibular lobe (90) is positioned substantially nearer to the distal end of the blade than is the lingual lobe (100). Other embodiments of this spatula and blade are provided.

Other embodiments provide for devices comprising a frame and a spatula having the characteristics described herein.

Still other embodiments provide for improvements to the devices described in U.S. Pat. No. 5,897,491, including expanding the transverse struts of the frame and repositioning the knob for controlling the movement of the spatula.

Still another embodiments provide for systems for conducting transoral surgery, including TORS, which comprise any one of the embodied spatulas or devices, as described herein.

Still other embodiments provides for the use of a spatula, device, or system described herein for the use in performing transoral examination or surgery on a patient.

BRIEF DESCRIPTION OF THE DRAWINGS

FIGS. 5, 5A, and 5B shows additional oblique views of spatulas of the instant invention.

DETAILED DESCRIPTION OF ILLUSTRATIVE EMBODIMENTS

The present invention may be understood more readily by reference to the following detailed description taken in connection with the accompanying Figures, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the method of making and using articles and to the resulting, corresponding physical articles themselves, as well as the referenced and readily apparent applications for such articles.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When values are expressed as approximations by use of the antecedent "about," it will be understood that the particular value forms another embodiment. In general, use of the term "about" indicates approximations that can vary depending on the desired properties sought to be obtained by the disclosed subject matter and is to be interpreted in the specific context in which it is used, based on its function, and the person skilled in the art will be able to interpret it as such. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, reference to values stated in ranges include each and every value within that range.

One embodiment of this invention provides a spatula for use in surgery or examination via the oral cavity comprising: (a) a handle (10), having proximal and distal ends and a longitudinal axis between the ends; (b) a blade (20) having top and bottom surfaces, a proximal end (30), a distal end (40), and opposing lingual (50) and mandibular (60) edges; the distance between the proximal and distal edges defining blade length; the distance between opposing lingual and mandibular edges defining blade width; wherein (i) the proximal end of the blade being attached to the distal end of the handle, either directly or through use of a spacer, the entire assembly having a major longitudinal axis (70) parallel to the longitudinal axis of the handle and extending along the length of the blade; (ii) the blade being upwardly concave across the width, having a centerline (80) at the lowest line of concavity along the blade; (iii) the blade containing a region of curvature along its length, such that the blade depends downward while maintaining the upwardly concave curvature across the width; and (iv) each of the lingual and mandibular edges having a lobed protrusion, each lobe having a point of maximum lateral displacement from the body of the blade, asymmetrically displaced with respect to one another along the length of the blade, such that the mandibular lobe (90) is positioned substantially nearer to the distal end of the blade than is the lingual lobe (100).

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Finally, while an embodiment may be described as part of a series of steps or part of a more general composition or structure, each said step may also be considered an independent embodiment in itself. As an example of the second of these principles, another embodiment provides a spatula for use in surgery or examination via the oral cavity comprising: (a) a handle (10), having proximal and distal ends and a longitudinal axis between the ends; (b) a blade (20) having top and bottom surfaces, a proximal end (30), a distal end (40), and opposing lingual (50) and mandibular (60) edges; the distance between the proximal and distal edges defining blade length; the distance between opposing lingual and mandibular edges defining blade width; wherein the proximal end of the blade being attached to the distal end of the handle, either directly or through use of a spacer, the entire assembly having a major longitudinal axis (70) parallel to the longitudinal axis of the handle and extending along the length of the blade; and comprising at least one but not all of the following features: (i) the blade being upwardly concave across the width, having a centerline (80) at the lowest line of concavity along the blade; (ii) the blade containing a region of curvature along its length, such that the blade depends downward while maintaining the upwardly concave curvature across the width; (iii) a lingual lobe; and/or (iv) a mandibular lobe, and where both the lingual and mandibular lobes are present, they are arranged as described in the preceding paragraph, such that the mandibular lobe (90) is positioned substantially nearer to the distal end of the blade than is the lingual lobe (100).

The terms used within this application are generally given their normal interpretation so as to be understood by one skilled in the art of medical devices or transoral examination or surgery. Certain specific terms are defined herein for sake of added clarity. For example, use of the terms "lingual" and "mandibular" are not necessarily intended to be limiting with respect to the blade, though one may envision, when a spatula blade is placed in the mouth of a patient, the lingual edge and/or lobe rests against the tongue of the patient, and the mandibular edge and/or lobe rests against the oral cavity adjacent to the lower jaw.

In certain embodiments, the blades are asymmetrically configured, having no axes or points of symmetry. Non-limiting examples of such spatulas can be seen in FIGS. 3-6. Applying an analogy found in organic chemistry, the blades may be envisioned as being "chiral," having a left-handed and right-handed orientation, though these descriptions are used mainly when comparing blades of opposite symmetry. In this regard, use of the "matched pair," in the context of the blades, is intended to connote two spatula blades, each of which has the characteristics of a spatula blade within the scope of the present invention, but which differ in their specific orientation ("handedness"). Non-limiting examples of such pairs can be seen in FIG. 3 and FIG. 5. Further extending the analogy to organic enantiomers, one spatula of a matching pair may be described as practically a mirror image of the other, where the term "mirror image" will be understood by one skilled in the art to reflect left- and right-handedness of an analogized enantiomeric pair. While the definition of the term "practically" includes it ordinary meaning, that meaning, in this context, also describes any unintentional or intentional non-substantive differences between the two spatulas within a matched pair, for example resulting from manufacturing or machining variances. The term "non-substantive" in this context refers to having no real impact on functionality for the intended use. For example, an engraved marking may be considered an intentional, non-substantive difference.

Also, at various points of the following discussion, it may be useful to envision the blade as positioned on a three axis Cartesian coordinate system, where the longitudinal axis lies substantially along an x-axis, the lateral width substantially defines a y-axis (or x-y plane), and the concept of top-bottom or up-down substantially defines the z-axis (or x-z or y-z plane).

FIGS. 3-6 all show various illustrative embodiments of the present invention. FIG. 4 shows such embodiments labeled as described herein. While not intending to limit the scope of the invention, reference to this Figure will provide the reader with a better appreciation of the discussion herein.

Referring first to the handle, in various embodiments, the handle comprises a structure containing a means for allowing a user to provide controlled incremental movement of the spatula into mouth of the patient along the longitudinal axis of the handle, when attached to a holder device designed for this purpose (for example, such as one of the retractors described above, or as described in the '491 patent). In various embodiments, this is achieved by providing mechanical threads or ratcheting teeth along at least a portion of the handle, such that when mated with corresponding threads or teeth on a fixture, can provide controlled movement. One such description of this control mechanism can be found in the '491 patent cited above. In other embodiments, the handle may be devoid of such mechanical threads or ratcheting teeth, wherein such incremental movement may be achieved by other means, for example by inserting a smooth or patterned handle into a sleeve or similar device containing such mechanical threads or ratcheting teeth. These mechanical threads or ratcheting teeth may be provided anywhere on the top, bottom, or side surfaces of the handle as convenient for manufacture or design, but are usually applied to a broad surface, preferably a top or bottom surface, more preferably to the bottom surface, as illustrated herein. While the various embodiments shown in the accompanying Figures show ratcheting teeth along the entire length of the bottom surface of the handle, it is not necessary that such teeth (or threads) cover the entire (bottom) surface, so long as they are sufficient to provide the range of motion desired for their purpose.

In various embodiments, the handle is attached to the blade as shown in FIGS. 3-6; that is, the top surface of the distal end of the blade is attached to the bottom surface of the proximal end of the blade, using an interposing spacer. In other embodiments, no spacer is applied. In still other embodiments, the relative positions of the handle and blade are reversed, such that the bottom surface of the distal end of the blade is attached to the top surface of the proximal end of the blade, either with or without an interposing spacer. In still other embodiments, the distal end of the handle abuts and/or is attached to the proximal end of the blade, providing for a unitary body. This concept is illustrated in the prior art spatulas of FIGS. 1 and 2, where the handle and blade provide a continuous handle-blade configuration.

In still other embodiments, the functions of the handle are integrated into the blade itself, so that a portion of the proximal end of the blade may be described as or considered the handle, containing the features associated with the handle. In these embodiments, the "spatula" is defined by the descriptions applied to the term "blade" as provided herein. Stated in another way, in certain of these embodiments, the blade itself may be considered a spatula within the scope of this invention.

In various embodiments, the length of the blade is in the range of between about 3 inches (about 7.6 cm) and about 7 inches (about 17.8 cm), in the range of between about 3.5 inches (about 8.9 cm) and about 4.5 inches (about 11.4 cm), and in the range of between about 5 inches (about 12.7 cm) and about 6 inches (about 15.2 cm), in each case exclusive of the length of the handle. These lengths allow the spatula-blade assemblies to be used in modified retractor frames and allow closer approach by robotic camera so as to allow a view into the patient's mouth when the retractor is in place.

Figure 4A:
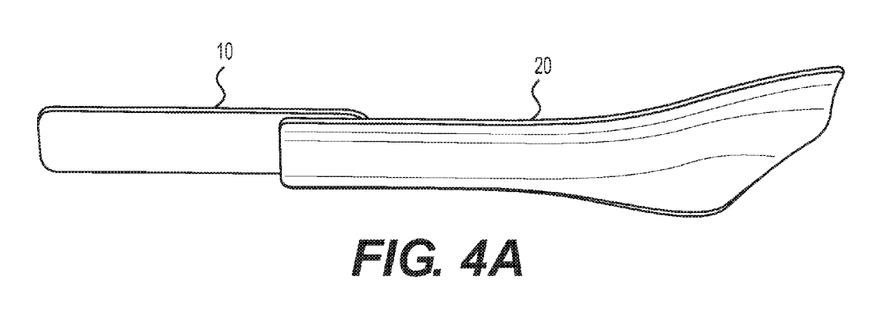
FIG. 4A-D show several embodiments of the present invention, presented as an oblique angle, and labeled according to the descriptions of the specification.
Figure 4B:
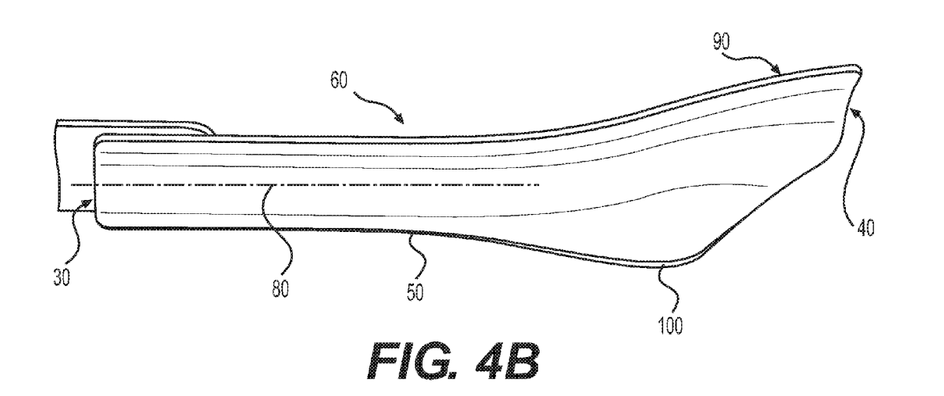
Figure 5:
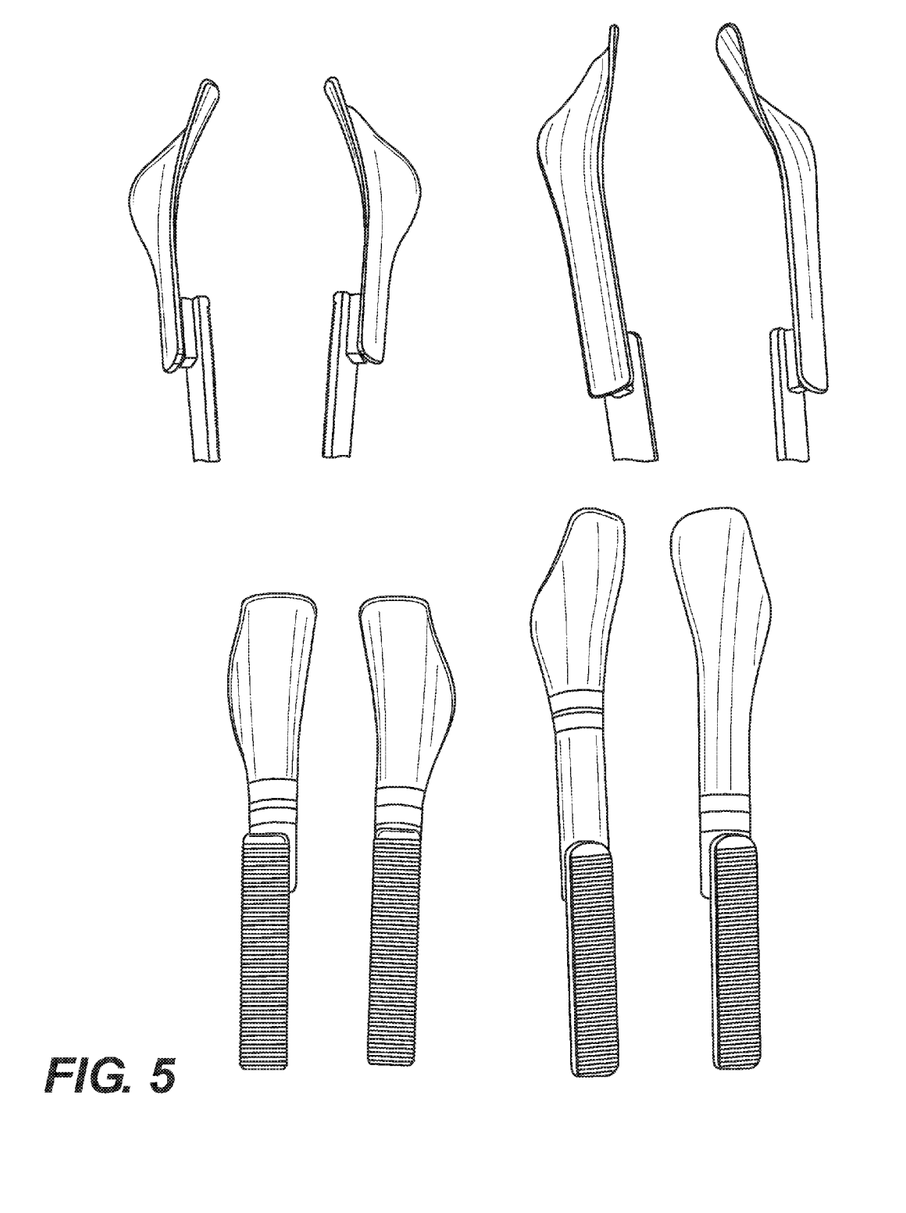
Figure 6A:
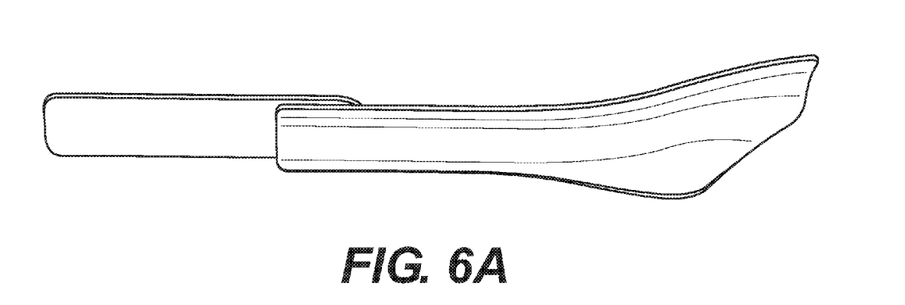
FIGS. 6A-D show additional oblique views of spatulas of the instant invention.
Figure 6B:
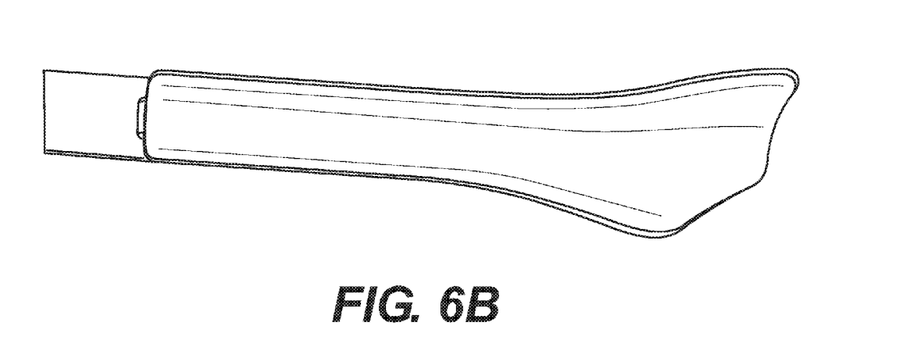
Figure 6C:
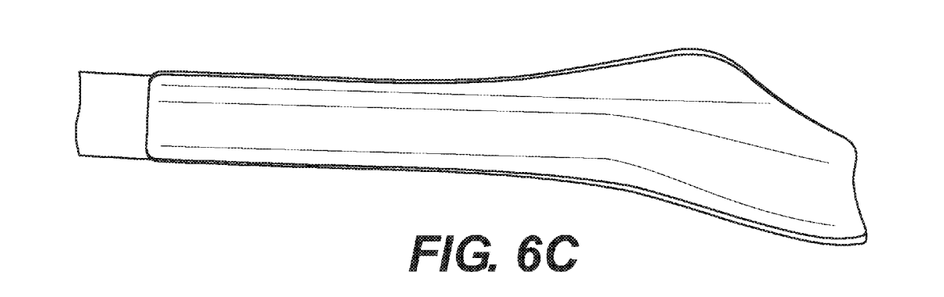
Figure 6D:
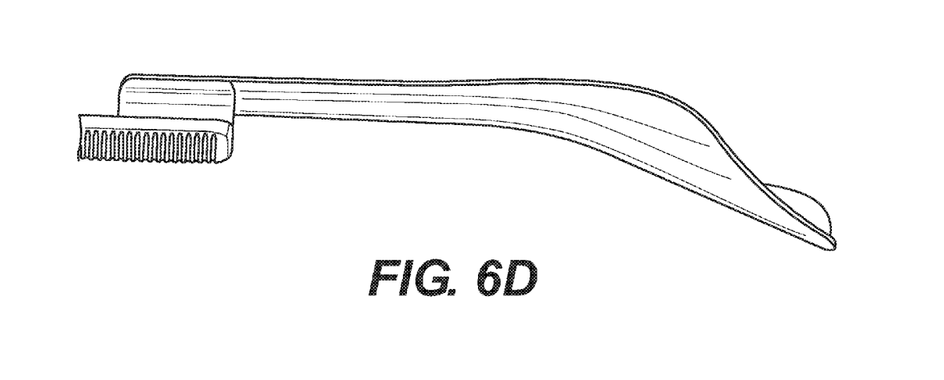
Figure 8A:
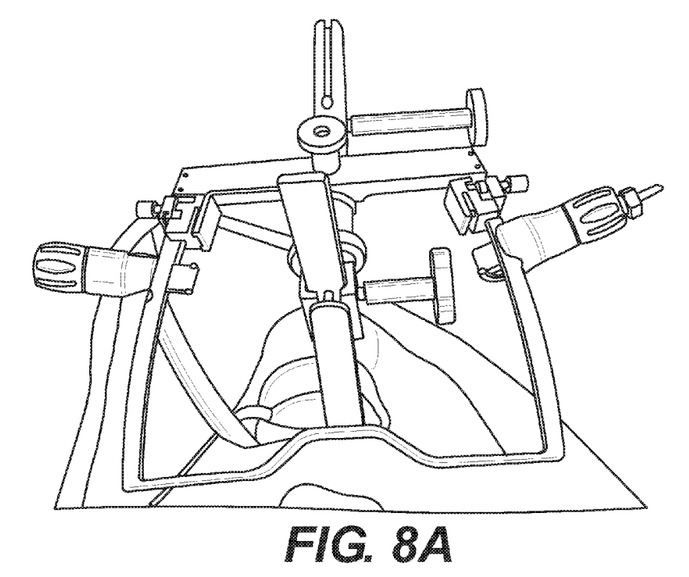
FIGS. 8A and 8B illustrate the use of the frame as applied to a patient undergoing TORS.
Figure 8B:
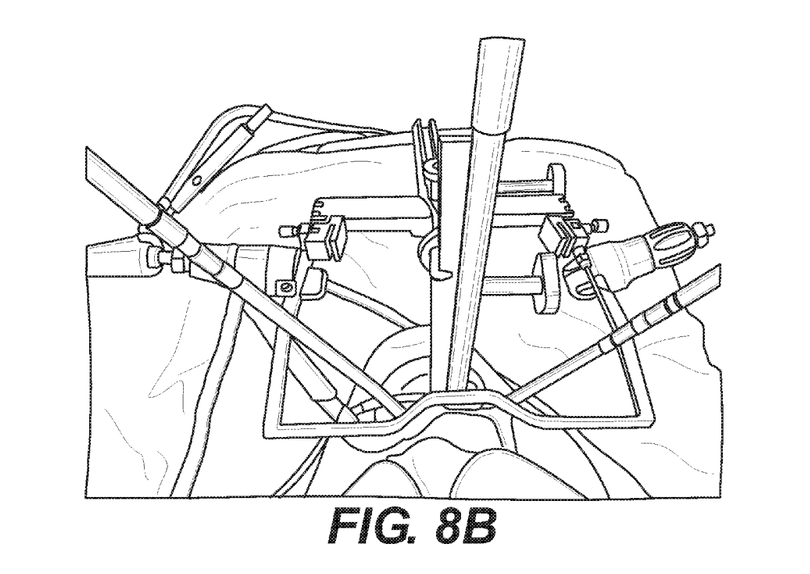

Referring next to the lateral dimension, various embodiments of the blade are described as upwardly concave across the width (or lateral axis), having a centerline at the lowest line of concavity along the blade. The concept of a centerline axis is shown in FIG. 4B. This concavity helps provide room for the robotic arms and the tips of the instruments to access the transoral regions of interest (see, e.g., FIG. 8). In various embodiments, the upward concavity is defined the arc of a circle having a radius in the range of between about 1 m and 10 mm, in the range between about 1 cm (about 0.4 inch) and about 10 cm (3.9 inch), in the range of between about 2 cm (about 0.8 inch) and about 8 cm (3.1 inch), in the range of between about 3 cm (about 1.2 inch) and about 7 cm (about 2.8 inch), in the range of between about 3.5 cm (about 1.4 inch) and about 6.5 cm (about 2.6 inch), or in the range of between about 4 cm (about 1.6 inch) and about 6 cm (about 2.4 inch). This degree of concavity can be constant or vary along the longitudinal axis.

Referring next to the longitudinal dimension, it is convenient to consider the assembly in terms of the major longitudinal axis (70) described above—i.e., parallel to the longitudinal axis of the handle and extending along the length of the blade—and the centerline (80) of the blade. In some embodiments, the curvature of the blade may reflect an increasing lateral departure (i.e., within the x-y plane of the hypothetical Cartesian coordinate system) from the major longitudinal axis as one progresses along the blade toward the distal end. In some embodiments, this departure is slight, with specific embodiments showing less than 10%, less than 5%, less than 1% deviation from the major longitudinal axis (70) in the x-y plane, with deviation defined as the ratio of the distance of maximum deflection to the total length of the axis. In other preferred embodiments, this departure is practically non-existent.

By contrast, preferred embodiments of the invention provide that the blade contains a region of curvature along its length, such that the blade depends downward (i.e., in the x-z plane) while maintaining the upwardly concave curvature across the width. This curvature is present to reflect the anatomic characteristics of a patient's transoral cavity. In some embodiments, this region of curvature of is centered between about 20 and about 80% of the longitudinal distance of the blade, when measured either from the proximal or distal end of the blade. More preferably, this region of curvature is centered between about 30% and about 70% of the longitudinal distance of the blade.

Figure 4C:
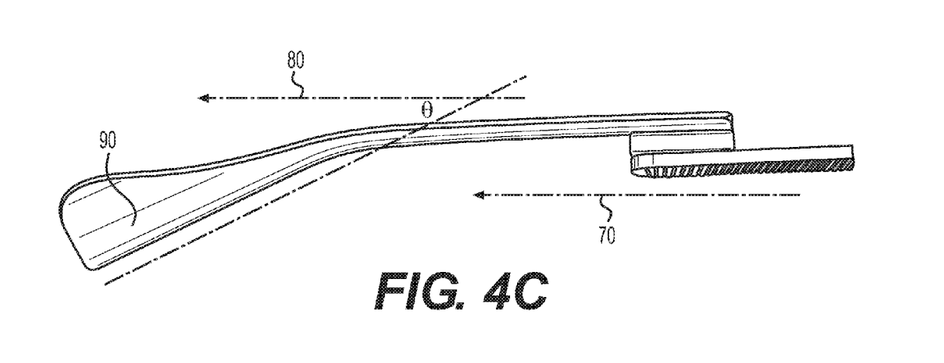

This curvature does not necessarily extend along the entire length of the blade. Instead, certain embodiments provide that this curvature simply provides a gradual transition for two, otherwise linear (in the x-z plane) lines of the blade. That is, in various embodiments, the portions of the centerline of the blade between the proximal edge and this region of curvature and between the distal edge of the blade and the region of curvature are substantially straight lines (in the x-z plane). This concept is illustrated in FIG. 4C, wherein the thinner solid line labeled centerline axis represents the substantially linear portion (in the x-z plane) of the centerline of the blade between the proximal edge and this region of curvature and the dashed line represents the substantially straight line between the distal edge of the blade and the region of curvature (in the x-z plane). In a preferred embodiment, the substantially linear portion of the centerline of the blade between the proximal edge and this region of curvature is substantially parallel to the major longitudinal axis (70). In any case, the substantially straight lines defined on either side of the region of curvature define an angle θ. In separate preferred embodiments, this angle θ is in the range of between about 10° and about 40°, in the range of about 10° and 30°, and about 20°.

In describing these features in more absolute terms, in certain embodiments, the length of the blade having this substantially straight line (in the x-z plane) between the distal end and this region of curvature is in the range of between about 2.5 cm (about 1 inch) and about 6 cm (about 2.4 cm), in the range of between about 3 cm (about 1.2 inch) and about 5 cm (about 2 cm), and in the range of between about 3.5 cm (about 1.4 inch) and about 4.5 cm (1.8 inch).

As used to describe this feature, the term "substantially straight" is intended to recognize that the realities of manufacturing may provide for slight curvatures of even otherwise straight lines. Accordingly, even those blades wherein the nominally linear portions on either side of the region of curvature deviate from pure linearity by less than 10%, by less than 5%, or by less than 1% along the centerline in the x-z plane are taken to be substantially straight in this dimension.

Turning next to the features on the lateral or lingual and mandibular edges, in various embodiments, one or both of the lingual and mandibular edges has a lobed protrusion, each lobe having a point of maximum lateral displacement from the body of the blade. Where both lingual and mandibular lobes are present, they are asymmetrically displaced with respect to one another along the length of the blade, such that the mandibular lobe (90) is positioned substantially nearer to the distal end of the blade than is the lingual lobe (100). These lobes preferably maintain the lateral curvature as described above. In some embodiments, the mandibular lobe is substantially adjacent to the distal end of the blade and the lingual lobe is positioned closer to the proximal end. Again, these features are labeled as such in FIG. 4C and FIG. 4D, though contained in each of the embodiments shown in FIGS. 3-6. These nodes are especially distinguished in FIG. 3A and FIG. 3B. The designations "lingual" and "mandibular" edges and nodes reflect that these portions of the spatula blade are intended to be used to abut the tongue and jaw-line, respectively. The placement of these nodes results in a curvature of the blades which allow for maximum exposure to retract the tongue out of the way and also to allow for maximum room to admit the tips of the robotic arms transorally. The relative flatness (when viewed in the z-direction) of the mandibular edge may be seen to allow the user to avoid the lower jaw on the side of the lesion that is being removed when the blade is in place in the mouth. The relative curvature provided by the lingual node on the lingual edge helps push the tongue out of the way and provide room for the robotic arms, and still be small enough so it does not interfere with the robotic arms when they are in the mouth.

Figure 4D:
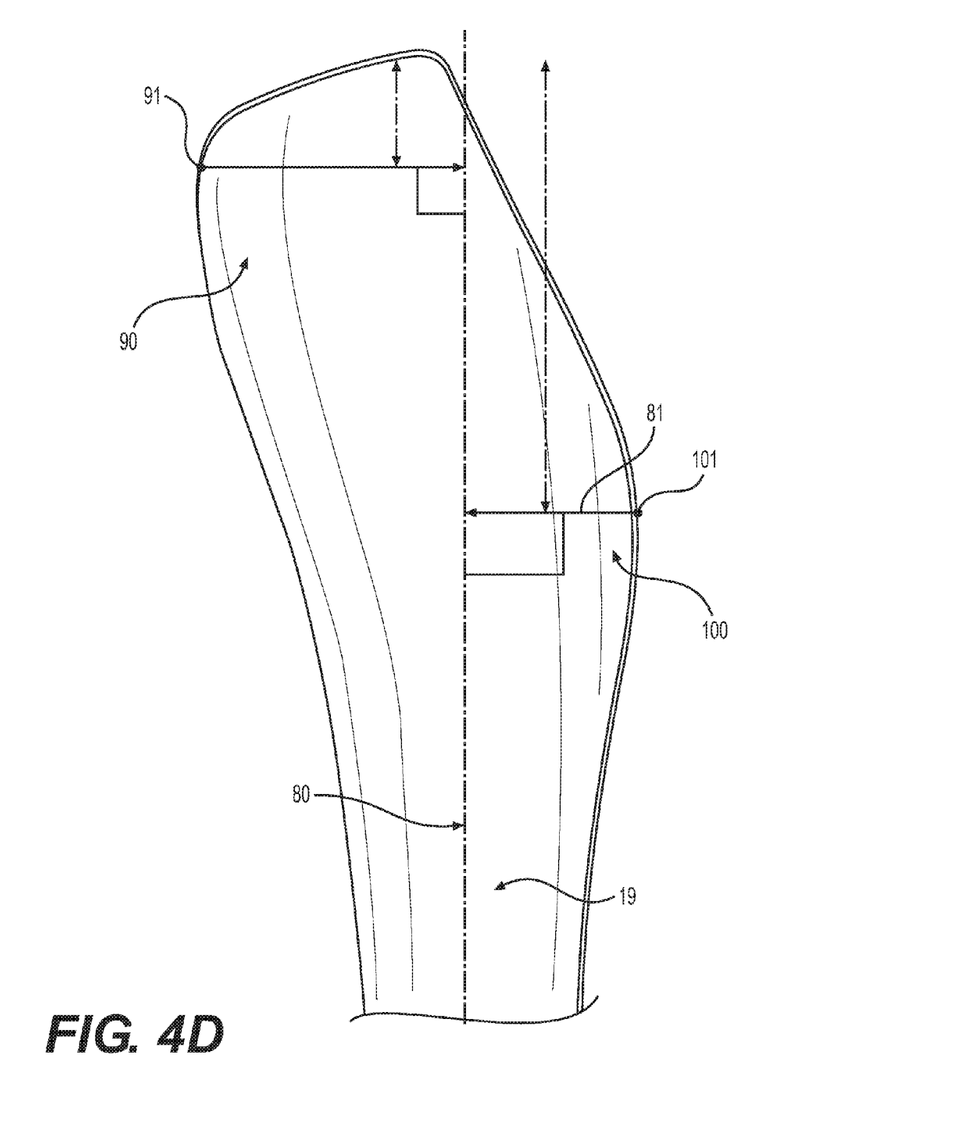

For purposes of description, these nodes (mandibular lobe/distal lobed protrusion 90 and lingual lobe/proximal lobed protrusion 100) are characterized as having points of maximum lateral displacement (91, 101, respectively) central longitudinal axis 80 of the blade (for one non-limiting example, see FIG. 4D). When described as a distance from the distal end of the blade, that distance refers to the distance between the distal end and a point on the centerline (e.g., see single headed arrows in FIG. 4D), corresponding to the shortest distance between the point of maximum lateral displacement and the centerline (e.g., see double-headed dotted arrows in FIG. 4D). In conjunction with the central longitudinal axis 80, the point of maximum lateral displacement 101 defines a lateral axis 81 that is perpendicular to the central longitudinal axis. Blade 20 also includes a shaft portion 19.

In various embodiments, the point of maximum lateral displacement for the lingual lobe is in the range between about 10% and about 50% or in the range of between about 20% and 40% of the longitudinal distance from the distal edge of the blade, relative to the entire length of the blade. Obviously, when described as a percentage displacement relative to the entire length of the blade, the actual value of displacement depends on the actual length of the blade. Accordingly, position of the lingual lobe can also be described in absolute terms, such that other embodiments describe the point of maximum lateral displacement for the lingual lobe as being in the range between about 0.5 inches (1.3 cm) and about 2.5 inches (6.4 cm), in the range between about 1 inch (2.5 cm) and about 2 inches (5.1 cm), and about 1.5 inches (3.8 cm), in each case from the distal end of the blade.

The point of maximum lateral displacement for the mandibular lobe, then, lies at a longitudinal position on the opposite side of the blade between the point of maximum lateral displacement for the lingual lobe and the distal end. In some embodiments, the point of maximum lateral displacement for the mandibular lobe is actually at the distal end, giving the visual impression of curvature to the entire blade assembly.

Turning next to the distal end of the blade, in various embodiments, the distal edge is substantially flat, relative to the body of the blade, when viewed from overhead, looking down on the top surface (i.e., looking along the arc radius of the lateral curvature). In other embodiments, this edge is concave; in still other embodiments, it is convex, when viewed along the same arc radius of the lateral curvature. The flat or concave configurations are preferred as to provide maximally broad exposure of the benign or malignant lesion during examination or surgery. The width of the distal edge is such as to allow for access into the oropharynx, larynx, or hypopharynx, and so is sized to allow for the anticipated variances of the anatomic features of the intended patient. In various embodiments, this width in the range of between about 0.5 (about 1.3 cm) and about 1.5 inches (about 3.8 cm), preferably about 1 inch (about 2.5 cm).

In each of the preceding embodiments, the spatula is adapted for use in transoral surgery or examinations, but preferably for transoral surgery, and more preferably for transoral robotic surgery. The term "transoral" connotes examination or surgery of or around the tongue, oropharynx, larynx, and oropharynx through the mouth. Attendant with this, additional adaptations of the spatula and/or blade are those required for use in surgery, including physical and chemical integrity, the ability to withstand practically used sterilization procedures, and the absence of sharp or non-rounded edges. In preferred embodiments, these spatulas and/or blades are comprise surgical and/or stainless steel. The blade thicknesses, combined with the materials of construction are such that the blades do not bend or distort when subjected to multiple surgeries. Typical thicknesses of the blades are on the order of 1-5 mm thick, typically 1-3 mm or 2 mm thick steel. In still other embodiments, the spatulas and/or blades are actually sterilized, so as to be useful in a surgical environment.

Manufacturing the spatulas/blades described herein is well within the capability of the skilled medical device machinist, using those methods conventionally used to make shaped medical tools.

The present invention also contemplates that these spatulas are provided as kits, and such kits are deemed within the scope of this invention. Additional embodiments provide that any one or more of the spatulas described herein may be packaged for delivery into a surgical environment, in container which ensure suitability for such an environment. For example, the spatulas or sets of spatulas may be encased by sealed plastic containers, including shrink-wrapped containers. The packages may comprise individual or multiple spatulas, the latter provided either as matched pairs, multiple match pairs, or multiple sets of left- or right-handed spatulas of differing embodiments. In this context, the term "differing embodiments" is intended to connote blades having different lengths or slightly different configurations, so as to allow for use in different procedures or with patients having different mouth shapes and sizes. In one embodiment, such a kit comprises at least two spatulas, comprising first and second spatulas, each spatula separately having the characteristics as described herein, but wherein the first and second spatulas are configured to be separately used in the left and right sides of a patient's mouth or throat. In other embodiments, the first and second spatulas are practically mirror images of one another, using the analogies and descriptions given above. In other embodiments, a kit comprises at least two spatulas, each spatula separately having the characteristics as described herein, and where the at least two spatulas are both configured to be used on the same side of a patient's mouth or throat.

In addition, the invention contemplates devices comprising these blades and/or spatulas. In particular, various embodiments of the present invention include those devices comprising a frame to which is attached a spatula or blade as described herein. Such embodiments include those devices comprising frames that are configured to be used as part of a retractor or mouth gag. In still other embodiments, the device comprises a frame configured to be used as part of a Feyh-Kastenbauer retractor, or FK retractor, as described in U.S. Pat. No. 5,897,491 (the "'491 patent"), which is incorporated by reference herein to describe this retractor. As used herein, the terms Feyh-Kastenbauer retractor or FK retractor refer to an embodiment described in this '491 patent, a commercial embodiment thereof, or a variant or improvement of such an embodiment as described herein. Such FK retractors are commercially available from Gyrus Medical GmbH, a division of Olympus, of Tuttlingen, Germany. That is, the present invention includes any embodiment of a device described in the '491 patent, when a spatula of the instant invention replaces to the lingual spatula of the '491 patent and is affixed to any of the frames described in the '491 patent.

The '491 patent describes one embodiment of the retractor as a "device (1) for endoscopic examinations and operations, comprising a (2) framework and at least one of holding means (32), connecting means (12; 83) and receiving means (20; 61a, 61b; 91; 111), for locking elements, spreading elements (8), lingual spatulas (15; 46a, 46b; 49; 52), labial-commissure spatulas (56a, 56b), lighting means (78), suction devices (104) for fluids including smoke, examining instruments, including endoscopes, surgical instruments, including grasping forceps (86) and laser instruments for laser surgery and laser coagulation, wherein said holding means (32), connecting means (12; 83) and receiving means (20; 61a, 61b; 91; 111) are arranged on the framework (2); and a toothed rack (28) with which the position of a column (21) bearing the receiving means (20) for the lingual spatula (15) is manually adjustable in relation to a guide element (22) of the attachment framework (2)," wherein the parenthetical numbers refer to elements defined in the '491 patent. The present invention includes embodiments wherein the spatulas described in the instant application and corresponding to the lingual spatulas of the '491 patent, are affixed to the '491 patent device.

In various embodiments, the spatula is affixed to a fixture on the device frame capable of incrementally moving and controlling the movement of the blade in the direction of the major longitudinal axis of the spatula or blade, optionally taking advantage of the mechanical threads or ratcheting teeth on the spatulas described above. In other embodiments, the handle of the spatula is mounted on an adjustable column of the device, the displacement of which is controlled by a rotatable shaft, described as element 46 in U.S. Pat. No. 5,897,491, wherein the control mechanism for the rotatable shaft is positioned to be within the spacing of the support struts, as shown in FIG. 7B. Contrast the position of this knob in the device shown as prior art in FIG. 7A with that of this invention shown in FIG. 7B.

Figure 7A:
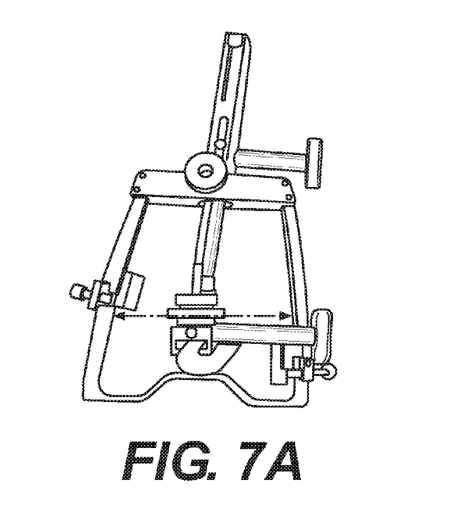
FIGS. 7A and 7B show two frames used for TORS. The frame in FIG. 7A is as historically commercially provided. The frame in FIG. 7B illustrates the improvements of the present invention, including the wider spacing of the frame and the shortening of the axis for controlling the movement of the spatula when attached to the frame.
Figure 7B:
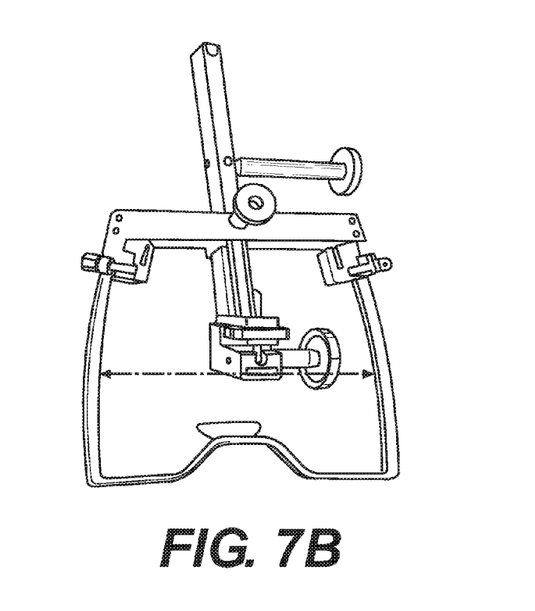

In addition to those frames historically provided, such as shown in FIG. 7A and described in "FK laryngo-pharyngo-scope" published by the ENT-Group, and available from gyrusmedical.de, the present invention also includes those embodiments wherein the blades described herein are attached to a frame of a substantially quadrilateral arrangement of support struts, and wherein one pair of opposing support struts has an internal spacing of at least about four inches (about 10.2 cm), at least about five inches (about 12.7 cm), or about 6 inches (about 15.2 cm), where this spacing spans, or superposes, the space of the mouth of the intended patient. Such an arrangement of the latter embodiment is shown in FIG. 7B (where the internal spacing is along the dotted line). The term "substantially quadrilateral" refers to a structure, having four support struts arranged in a four-sided arrangement, such as shown in FIG. 7, wherein at least one support strut is or may be curved. Commercial embodiments historically have had a maximum spacing on the order of about 4 inches (about 10.2 cm), in the region spanning that where the spatula is mounted to enter the mouth (e.g., corresponding to the dotted line in FIG. 7A). As described in the Background section above, this spacing was inadequate for use in TORS, owing to the insufficient spacing for instruments. For example, see FIG. 8B for the preferred placement of surgical instruments. An increased spacing of at least about five inches (about 12.7 cm), or at least about 6 inches (about 15.2 cm) provides to the use of the frame and spatula in TORS. The increased spacing allows for the frame to attach a number of instruments, the shape, size and number of those attachments have been significantly altered to allow for use during Transoral Robotic Surgery (TORS). Again, and in particular, the shape of the spatula blades have been significantly changed giving access to the robotic arms during Transoral Robotic Surgery (TORS).

For the sake of clarity, embodiments comprising the frame containing a substantially quadrilateral arrangement of struts, otherwise configured to be used as part of a Feyh-Kestenbaum-type retractor, but having the increased spacing of at least about five inches (about 12.7 cm), or about 6 inches (about 15.2 cm) are considered to be independent embodiments within the scope of the present invention, whether or not a blade or spatula of the present invention is attached thereto. Separately, in other embodiments, the length of the rotatable shaft, functionally described as element 43 in U.S. Pat. No. 5,897,491, but as shown in FIG. 7B—i.e., positioned to be within the spacing of the support struts—is considered yet another embodiment of the present invention, whether or not a blade or spatula of the present invention is attached the corresponding adjustable column.

These embodiments which may be seen as improvements or alterations of the devices described in U.S. Pat. No. 5,896,491—i.e., expanding the width of the frame and re-sizing the length of the rotatable shaft 43 and re-positioning the control knob 41 for that shaft—are to be seen as described in the context of the description provided by the text of the '491 patent, which again is incorporated by reference herein. In one non-limiting example, one embodiment of the present invention described using this reference is a device as described in claim 1 of U.S. Pat. No. 5,896,491, said framework (2) having vertical (3a and 3b) and horizontal struts (as shown in FIG. 1 of that '491 patent), the spacing between the vertical struts defined by the length of a constructed line between these struts and passing adjacent to the column (21) bearing the receiving means (20), wherein the spacing between the vertical struts of the framework has a spacing of at least about five inches or at least about 6 inches (the labeling numbers in this description corresponding to those in the '491 patent). Similarly, another embodiment comprises a device otherwise described in the '491 patent except wherein the shank 43 has a length that is less than one half of the spacing between the two transverse frame-elements 3a, 3b, so that the knurled screw 41 lies inside the transverse frame elements.

In addition, the invention further contemplates those systems for conducting transoral robotic surgery which comprise any one of the embodied spatulas or devices, as described herein. The Da Vinci Surgical System, marketed by Intuitive Surgical, Inc. of Sunnyvale, Calif., in one system presently used for oral and laryngopharyngeal surgeries. A procedural guide describing some embodiments of such a system is available at uphs.upenn.edu in. Those systems incorporating any one of the embodied spatulas or devices, as described herein, are seen as embodiments within the scope of this invention.

Still another series of embodiments of the present invention including performing transoral examination or surgery on a patient using any one of the embodied spatulas, blades, devices, or systems as described herein. More specific embodiments include those where the spatula, device, or system described herein is used in performing transoral surgery on a patient, and those where the transoral surgery involves surgery in the region of the oral cavity (including lesions in the area of the tongue), oropharynx, larynx, and hypopharynx, including transoral laser and/or robotic surgery of these regions.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article.

The disclosures of each patent, patent application, and publication cited or described in this document are hereby incorporated herein by reference, in their entirety.

What is claimed:

1. A spatula for use in oral surgery or oral examination comprising:

a blade elongate along a central longitudinal axis, the blade having a top surface, a bottom surface opposite the top surface, a proximal end, a distal end spaced from the proximal end along the central longitudinal axis so as to define a length of the blade, a lingual edge and a mandibular edge spaced from the lingual edge so as to define a blade width perpendicular to the central longitudinal axis, the width extending between the mandibular edge and the lingual edge, the central longitudinal axis positioned equidistantly between the lingual edge and the mandibular edge at the proximal end of the blade, and the top and bottom surfaces of the blade extending between the proximal end, the distal end, the mandibular edge, and the lingual edge of the blade, wherein:

i. at least a portion of the top surface is concave along the width of the blade, such that at least a portion of the mandibular edge and at least a portion of the lingual edge are disposed in a different plane relative to the at least a portion of the top surface;

ii. the bottom surface defines a region of curvature along the length between the proximal and distal ends of the blade, such that the distal end of the blade depends downward along the central longitudinal axis with respect to the proximal end of the blade;

iii. the lingual edge having a proximal lobed protrusion and the mandibular edge having a distal lobed protrusion, wherein the proximal lobed protrusion disposed closer to the proximal end than the distal lobed protrusion and each of the proximal and distal lobed protrusions have a point of maximum lateral displacement from the central longitudinal axis, said lobed protrusions being asymmetrically displaced with respect to one another along the central longitudinal axis; and iv. the distal end includes an edge defined between the top and bottom surfaces of the blade that extends from the central longitudinal axis towards the distal lobed protrusion, at least a portion of the distal end edge extending linearly from the central longitudinal axis to the distal lobed protrusion.

2. The spatula of claim 1, further comprising a handle at the proximal end of the blade, the handle having mechanical threads or ratcheting teeth.

3. The spatula of claim 1, wherein the region of curvature is centered in a range between 20% and 80% of the length of the blade, when measured from either the proximal or distal ends of the blade.

4. The spatula of claim 3, wherein the region of curvature is centered in a range between 30% and 70% of the length of the blade, when measured from either the proximal or distal ends of the blade.

5. The spatula of claim 4, wherein the region of curvature depends downward with respect to the proximal end of the blade at an angle, $\theta$, where $\theta$ is in a range between about 10° and about 40°.

6. The spatula of claim 5, wherein angle $\theta$ is in a range of between about 10° and about 30°.

7. The spatula of claim 6 wherein angle $\theta$ is about 20°.

8. The spatula of claim 1, wherein the distal lobed protrusion is substantially adjacent to the distal end of the blade.

9. The spatula of claim 1, wherein the point of maximum displacement of the proximal lobed protrusion, as positioned along the central longitudinal axis, is in a range of between 10% and 50% of the length from the distal end of the blade, relative to an entire length of the blade along the central longitudinal axis.

10. The spatula of claim 9, wherein the point of maximum displacement of the proximal lobed protrusion, as positioned along the central longitudinal axis, is in a range between 20% and 40% of the length from the distal end of the blade, relative to an entire length of the blade along the central longitudinal axis.

11. The spatula of claim 1, wherein the point of maximum displacement of the proximal lobed protrusion, as positioned along the centerline, is in a range between 0.5 inches and 2.5 inches from the distal end of the blade.

12. The spatula of claim 11, wherein the point of maximum displacement of the proximal lobed protrusion is in a range between 1 inch and 2 inches from the distal end of the blade.

13. The spatula of claim 12, wherein the point of maximum displacement of the proximal lobed protrusion is approximately 1.5 inches from the distal end of the blade.

14. The spatula of claim 1, wherein the length of the blade is in a range of between 3 inches and 7 inches.

15. The spatula of claim 14, wherein the length of the blade is in a range of between of 3.5 inches and 4.5 inches.

16. The spatula of claim 14, wherein the length of the blade is in a range of between 5 inches and 6 inches.

17. The spatula of claim 1, wherein the width of the distal end of the blade is in a range of between 0.5 inches and 1.5 inches.

18. The spatula of claim 17, wherein the width of the distal end of the blade is about 1 inch.

19. The spatula of claim 1, wherein the spatula is adapted for use in surgery performed via the oral cavity.

20. The spatula of claim 19, wherein the spatula is adapted for use in robotic surgery performed via the oral cavity.

21. The spatula of claim 20, wherein the transoral robotic surgery involves surgery in the region of the oral cavity, oropharynx, larynx, and hypopharynx.

22. The spatula of claim 1, wherein the spatula is sterilized.

23. The spatula of claim 1, wherein the blade a shaft portion that includes the proximal end,
   at least a portion of the top surface is concave along a width of the shaft portion of the blade, and
   the blade depends downward at the region of curvature with respect to the shaft portion of the blade.

\* \* \* \* \*